(12) United States Patent
Gauchet

(10) Patent No.: US 6,820,313 B2
(45) Date of Patent: Nov. 23, 2004

(54) METHOD OF MANUFACTURING AN ULTRASOUND TRANSDUCER AND ULTRASOUND TRANSDUCER OBTAINED BY MEANS OF THE METHOD

(75) Inventor: Maurice G. Gauchet, Asnieres sur Seine (FR)

(73) Assignee: Koninklijke Philips Electronics N.V., Eindhoven (NL)

(*) Notice: Subject to any disclaimer, the term of this patent is extended or adjusted under 35 U.S.C. 154(b) by 357 days.

(21) Appl. No.: 10/072,113

(22) Filed: Feb. 8, 2002

(65) Prior Publication Data
US 2002/0124369 A1 Sep. 12, 2002

(30) Foreign Application Priority Data
Feb. 9, 2001 (EP) .......................... 01 400353

(51) Int. Cl.$^7$ .................. H04G 17/00; H01P 11/00; H01Q 13/00; H01L 41/04; H01L 41/08
(52) U.S. Cl. .................. 29/25.35; 29/594; 29/609.1; 310/334; 310/367; 310/369
(58) Field of Search .................. 29/25.35, 600, 29/738, DIG. 1, DIG. 3, 609.1, 595, 594; 310/364–371, 334, 363; 156/256–266; 73/702, 703

(56) References Cited

U.S. PATENT DOCUMENTS

| | | | | |
|---|---|---|---|---|
| 3,325,780 A | * | 6/1967 | Horan | 367/164 |
| 3,732,535 A | | 5/1973 | Ehrlich | 340/10 |
| 4,754,441 A | * | 6/1988 | Butler | 367/157 |
| 4,868,447 A | * | 9/1989 | Lee et al. | 310/328 |
| 5,241,235 A | * | 8/1993 | Culp | 310/328 |
| 5,412,854 A | * | 5/1995 | Lockwood et al. | 29/25.35 |
| 5,780,745 A | * | 7/1998 | Durand | 73/702 |
| 6,029,113 A | * | 2/2000 | Woodall | 702/1 |
| 6,190,497 B1 | * | 2/2001 | Chan et al. | 156/580.1 |
| 6,239,533 B1 | * | 5/2001 | Burov et al. | 310/328 |
| 6,362,559 B1 | * | 3/2002 | Boyd | 310/359 |

FOREIGN PATENT DOCUMENTS

JP 05-276594 * 10/1993

OTHER PUBLICATIONS

"Feasibility of Using Ultrasound Phased Arrays for MRI Monitored Non–Invasive Surgery" by Kullervo HYNYNEN et al., in IEEE Transactions of Ultrasonics, Ferroelectrics, and Frequency Control, vol. 43, No. 6, Nov. 1996.

* cited by examiner

Primary Examiner—Peter Vo
Assistant Examiner—Binh-An D. Nguyen
(74) Attorney, Agent, or Firm—John Vodopia

(57) ABSTRACT

A method of manufacturing an ultrasound transducer (60), which includes forming a plate into a hollow spherical cap by deformation, wherein the plate is initially in the form of a disc of a composite piezoelectric material. The step of forming is preceded by at least one slit (70) into the plate, wherein the at least one slit has a radial orientation and extends from the peripheral edge (72) of the disc (20) towards its center (C). After the step of forming, two facing, oppositely situated free edges (74, 76) which bound the slit (70) are substantially in contact with one another so as to minimize internal stresses in the cap caused by the deformation. A transducer obtained by such a method is also disclosed.

11 Claims, 2 Drawing Sheets

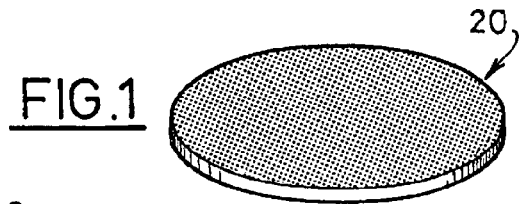
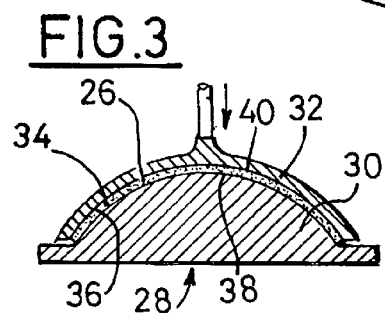
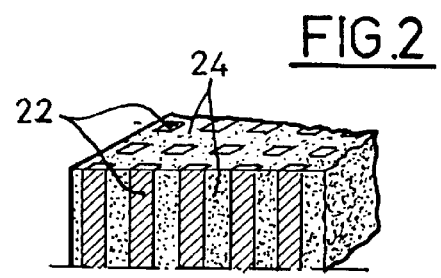
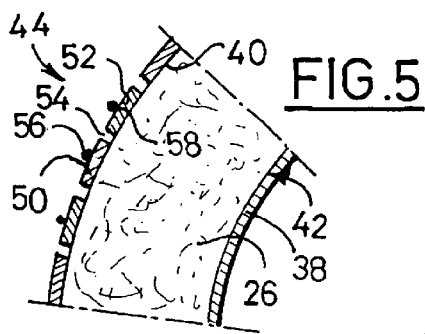
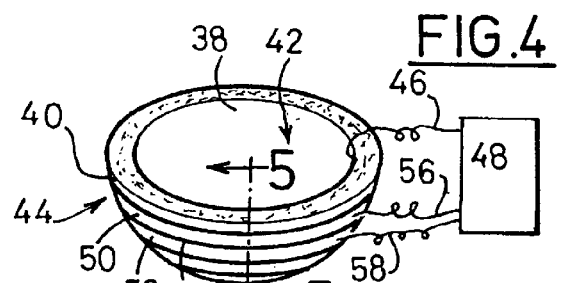
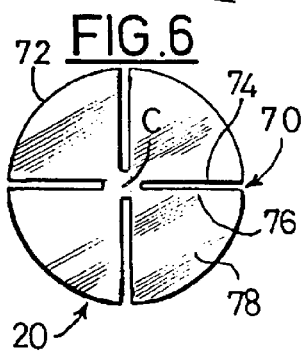
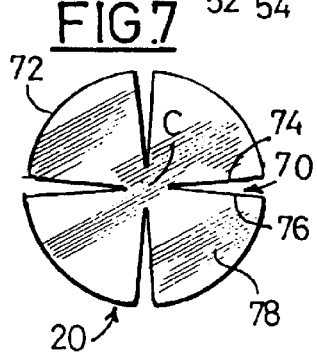
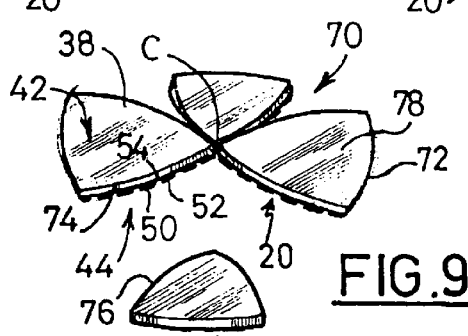
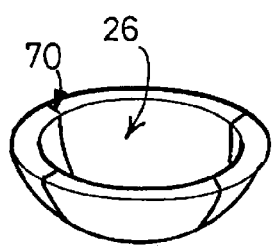

METHOD OF MANUFACTURING AN ULTRASOUND TRANSDUCER AND ULTRASOUND TRANSDUCER OBTAINED BY MEANS OF THE METHOD

The invention relates to a method of manufacturing an ultrasound transducer, which method includes a step of forming a plate which is shaped as a disc of a composite piezoelectric material into a hollow spherical cap.

Ultrasound transducers are used notably in the medical field. There are numerous applications for such transducers.

There are ultrasound transducers which operate with low powers, that is, of the order of a few hundreds of milliwatts for imaging, as well as so-called ultrasound power transducers which are capable, for example, of destroying tumors within the human body by raising the temperature; such transducers are powered by currents of the order of from one watt to some hundreds of watts.

Generally speaking, ultrasound transducers enable a given quantity of energy to be focused in a small zone which is referred to as the focal spot which has the shape of an ellipsoid. The focal spot corresponds to the zone of convergence of the ultrasonic radiation produced by the transducer. Generally speaking, the radiation propagates in a direction normal to the surface whereto it is applied. The radiation together forms a so-termed ultrasound beam. Thus, the ultrasound beam is generally oriented in the direction which corresponds to the symmetry axis of the spherical cap. Each transducer has a focal distance which corresponds to the distance between the focal spot and the apex of the spherical cap of the transducer. The focal distance of a transducer is determined in principle by its geometry, that is, notably by the radius of curvature of the spherical cap. Thus, with each specific geometry of the transducer there is associated a given focal distance which is referred to as the geometrical focal distance of the transducer. The shape of the focal spot is more elongate in the direction of the major axis of the ellipsoid as the focal distance is larger.

The ultrasound transducers are made of a piezoelectric material, that is, a material which is deformed when subjected to electric current pulses. The deformations of the material produce radiation in the range of ultrasound vibrations, which radiation propagates in water or liquids and converges towards the focal spot in which it causes notably a rise of temperature. In the case of ultrasound power transducers this rise in temperature suffices to burn tissue of the human body, notably tumors which may be malignant or non-malignant.

In order to optimize the treatment, it is important that the focal distance of the transducer used is short. Indeed, this enables the dimensions of the focal spot to be reduced, thus enhancing the precision of the treatment. On the other hand, when a tumor is situated at a small distance from the external surface of the skin of the patient, the transducer can then be arranged in the vicinity of the external surface of the skin. This volume of the device is thus reduced and the coupling between the transducer and the skin facilitated, thus optimizing the penetration of the energy into the body of the patient. The focal distance can be varied slightly by means of an electronic device which enables dephasing of the vibrations for given zones of the transducer so as to increase or decrease the focal distance of the transducer in relation to its geometrical focal distance. Variation of the focal distance enables displacement of the focal spot in order to enlarge the zone of treatment, that is, without displacement of the transducer. The thickness of the spherical cap determines the frequency of the ultrasound radiation.

A method of realizing a transducer in the form of a spherical cap is already known from the publication "Feasibility of Using Ultrasound Phased Arrays for MRI Monitored Non-Invasive Surgery" by Kullervo HYNYNEN et al., in IEEE Transactions on Ultrasonics, Ferroelectrics, and Frequency Control, vol. 43, No. 6, November 1996. This method utilizes a solid piezoelectric material in which a spherical cap of the desired dimensions is formed, notably a cap having the radius and thickness desired so as to obtain a given geometrical focal distance and radiation frequency. Subsequently, each spherical surface of the cap is covered with an electrode. When fed with an electric current, the electrodes enable the piezoelectric material to vibrate. Such a method is very expensive, because it requires a large quantity of piezoelectric material as well as exact machining operations. Moreover, the electronic device cannot be adapted so as to induce the dephasing of vibrations for given zones, so that the possibility of changing the focal distance of the transducer is lost.

It is also known to utilize composite piezoelectric materials which consist of a material which is formed by small elements of a piezoelectric material which are embedded in a matrix of an insulating material such as a polymer material. A disc of composite piezoelectric material is then formed, each surface of said disc being covered with an electrode which is realized by metallization in vacuum. When fed with an electric current, the electrodes enable the piezoelectric material to vibrate. The electrode on the rear surface of the disc consists of the juxtaposition of rings of a conductive material which are realized by photoengraving and chemical etching. The disc is thermodeformable because it consists of the polymer material. Thus, a hollow spherical cap is formed by deforming the disc under the influence of heat; this results in a shape having the desired radius of curvature.

However, the formation of the disc into a hollow spherical cap induces large mechanical stresses in the composite piezoelectric material, which stresses are larger as the radius of curvature of the ultrasound transducer is smaller.

During the operation of the transducer, the vibration at very high frequencies (of the order of from one to several MHz) of the piezoelectric elements also causes mechanical stresses inside the material.

The sum of the mechanical stresses must remain below the rupture strength limit of the composite piezoelectric material during use of the ultrasound transducer.

Thus, a method of this kind has its limitations when an ultrasound transducer having a small radius of curvature is to be realized. Indeed, for operation of an ultrasound transducer of a diameter of 100 mm and a thickness of approximately 1 mm at 1.5 MHz, the minimum radius of curvature which can be realized is of the order of 130 mm.

In order to solve these problems, the invention proposes a method of manufacturing an ultrasound transducer which includes a step of forming a plate which is shaped as a disc of a composite piezoelectric material into a hollow spherical cap as claimed in claim 1.

The invention also proposes an ultrasound transducer which is shaped as a hollow spherical cap manufactured by means of the above method.

The characteristics and advantages of the invention will be described in detail hereinafter with reference to the attached diagrammatic drawings; therein:

FIG. 1 is a perspective view of a disc of a composite piezoelectric material;

FIG. 2 is a partial radial cross-sectional view at an enlarged scale and in perspective of the disc shown in the foregoing Figure;

FIG. 3 is a sectional view of the device for forming the disc into a hollow spherical cap, realized in conformity with the present state of the art;

FIG. 4 is a perspective view of an ultrasound transducer realized by means of a method according to the present state of the art;

FIG. 5 is a partial sectional view at an increased scale, taken along the line 5—5 in the foregoing Figure;

FIG. 6 is a diagrammatic front view of a disc of a composite piezoelectric material after a step of cutting radial orientation slits in accordance with the invention;

FIGS. 7 and 8 are views similar to those of the foregoing Figure in which the slits are realized in conformity with alternative versions of the invention;

FIG. 9 is a perspective diagrammatic view of a disc of a composite piezoelectric material after a step of cutting radial orientation slits which extend as far as the center of the disc so as to separate it into several distinct portions;

FIG. 10 is a perspective diagrammatic view of a hollow spherical cap realized by means of the method in accordance with the invention;

Elements which are identical or similar will be denoted by the same reference numerals hereinafter.

Figure 11:
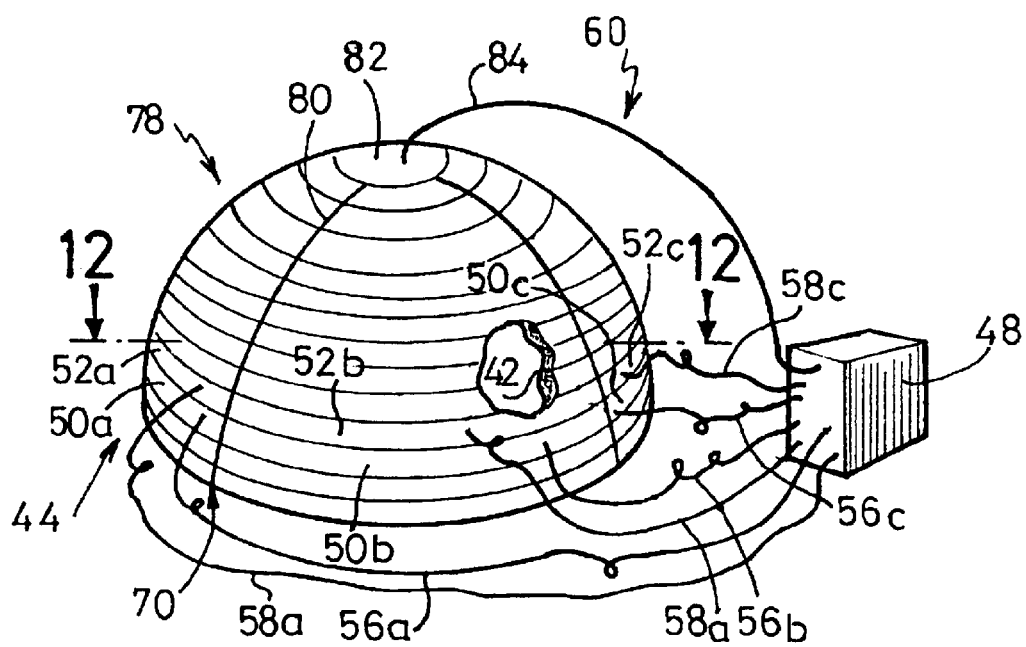
FIG. 11 is a diagrammatic view which shows an ultrasound transducer realized by means of the method of the invention.

FIG. 1 shows a disc 20 of a composite piezoelectric material. A material of this kind is formed by piezoelectric elements 22 which are shown in detail in FIG. 2 and are embedded in a material 24 which is electrically insulating such as epoxy resin. In the present example, the diameter and the thickness of the disc 20 are of the order of 120 mm and 2 mm, respectively. The piezoelectric elements 22 extend through the disc 20 in the axial direction and have a substantially square transverse cross-section whose sides amount to approximately 100 micrometers. They are regularly distributed in the material 24. Each of the two faces of the disc 20 is provided with an electrode 42, 44 which is realized by means of a known method as described above.

A hollow spherical cap 26 is realized by deformation of the disc 20. To this end, the disc 20 and its electrodes 42, 44 is arranged, as shown in FIG. 3, between two dies, that is, a lower die 30 and an upper die 42, of a forming device 28. The facing surfaces 34 and 36 of the lower die 30 and the upper die 32 define the spherical shape of the concave surface 38 and the convex surface 40 of the spherical cap 26. Thus, when the disc 20 is arranged between the two dies 30 and 32, the disc 20 is formed into a spherical cap 26 by bringing these two dies together in the axial direction.

The electrode 42, being deposited on the entire concave surface 38, is connected, by way of a conductive element 46, to the positive terminal of a current generator 48. The electrode 44, provided on the convex surface 40, in this case consists of the juxtaposition of rings of a conductive material, two of which are denoted by the reference numerals 50 and 52. In practice the electrode 44 is formed, for example, by fourteen rings. The rings 50, 52 are separated from one another by a hollow ring 54 which is shown in detail in FIG. 5. The ring 54 in an alternative version may be filled with an electrically insulating material, such as polyurethane varnish, in order to provide electrical insulation between the rings 50 and 52. Each ring 50, 52 is connected to the current generator via conductive elements 56 and 58 as shown in FIG. 4. The device thus realized forms an ultrasound transducer 60.

During the operation of the ultrasound transducer 60, the current generator 48 feeds the rings 50 and 52, causing vibration of the piezoelectric elements 22 with which they are in contact. When all rings of the electrode 44 are fed with a current of the same phase and amplitude, the focal spot is situated at the geometrical focal distance of the ultrasound transducer 60.

The current generator 48 may also supply the conductive elements 56 and 58 with currents of different phase and amplitude. This enables notably variation of the focal distance of the focal spot.

A device of this kind enables the realization of ultrasound transducers 60 with a large radius of curvature. Thus, it enables the realization of transducers which have a large focal distance.

However, such a method is inadequate when smaller geometrical focal distances are desired so as to treat tumors situated at a small distance from the surface of the skin of the patient and to enhance the precision of treatment.

Actually, in order to reduce the focal distance it is necessary to reduce the radius of curvature of the ultrasound transducer 60. However, the step of forming the disc 20 into a spherical cap 26 induces large stresses inside the composite piezoelectric material. For a given diameter of the transducer 60, the stresses are higher as the radius of curvature is smaller. This phenomenon is due to the greater deformation of the disc 20 of the composite piezoelectric material.

Actually, a first disc of a predetermined diameter is necessary so as to obtain a first spherical cap of a first diameter and a first radius of curvature. Similarly, in order to obtain a second spherical cap of a second diameter which is equal to the first diameter and a second radius of curvature which is larger than the first radius of curvature, it is necessary to form a second disc of the composite piezoelectric material which has a diameter larger than the predetermined diameter.

During the formation of the spherical cap, the peripheral length of the disc is reduced. The reduction of the peripheral length of the second disc is greater than the reduction of the peripheral length of the first disc. Consequently, the formation of the second spherical cap induces stresses, notably compressive stresses, which are greater than those introduced by the formation of the first spherical cap. When the radius of curvature of the spherical cap 26 is reduced below a predetermined value, which may be dependent on the diameter of the cap 26 and on its thickness, the stresses induced in the composite piezoelectric material of the cap 26 are too large and are liable to cause a rupture or malfunctioning of the transducer 60.

Actually, the sum of the stresses induced by the forming operation and the stresses produced by vibration of the piezoelectric elements 22 may cause fissures in the composite piezoelectric material, which fissures cause malfunctioning and/or rupture of the transducer 60. The sum of the stresses induced and the stresses produced by vibration of the piezoelectric elements 22 may also cause deformations of the spherical cap 26 which may lead to malfunctioning of the transducer 60.

In order to solve this problem, in accordance with the invention the step of forming the disc 20 of the composite piezoelectric material into a spherical cap 26 during the manufacture of the ultrasound transducer 60 is preceded by a cutting step which consists in the formation of at least one slit 70 which has a radial orientation and extends from the peripheral edge 72 of the disc 20 towards its center C in such a manner that, after the step of forming, the two oppositely situated, facing free edges 74, 76 which bound the slit 70 are substantially in contact with one another so as to minimize the internal stresses in the cap 26 which are caused notably by its deformation.

The FIGS. 6 to 8 show discs 20 of a composite piezoelectric material in which a number of slits 70 greater than one has been formed. In the example shown in the FIGS. 6 to 8, four slits 70 have been formed in conformity with three versions of the invention.

The slits 70 are preferably angularly distributed in a regular fashion so that they define substantially identical angular sectors 78. The slits 70 extend radially partly along radii of the disc 20. This enables a strong reduction of the stresses induced in the cap 26, however, while keeping the disc 20 in one piece, thus facilitating its positioning and retention in the forming device 28.

In conformity with FIG. 6 the oppositely situated free edges 74, 76 extend parallel to one another. They may be situated a few millimeters apart. Thus, the slits 70 of the discs 20 can be realized in the form of a saw cut whose thickness corresponds to the distance separating the free edges 74, 76.

In conformity with the version which is shown in FIG. 7, the oppositely situated, facing free edges 74, 76 have a radial orientation such that the corresponding slits 70 form a V whose apex is oriented towards the center C of the disc 20. The slits 70 can be realized by cutting by means of a water jet or by means of a wire saw, for example, a diamond type.

In accordance with FIG. 8, the oppositely situated free edges 74, 76 are curved and convex, their convexity being opposed. The exact shape of the oppositely situated free edges 74, 76 can be determined with precision by calculation on the basis of equations which are representative of the deformation of the disc 20 into a hollow spherical cap by way of approximative methods which consist notably in the determination of the width of the slits 70 for each specific diameter of the disc 20.

In conformity with a further version as shown in FIG. 9, the slits 70 extend radially as far as the center C of the disc 20 in such a manner that the angular sectors 78 are separated. This enables a further reduction of the internal stresses in the cap 26 which are caused by its deformation. In the example of FIG. 9, angular sectors 78 are separated into four distinct portions.

The free edges 74, 76 approach one another during the step of forming. The deformations also occur in the zones situated in the vicinity of the recessed radial end of the slits 70, that is, in such a manner that the cap 26 does not comprise any opening. In this stage various solutions are feasible.

The first solution consists in bringing the free edges 74, 76 into contact with one another. Upon cooling, the composite piezoelectric material hardens, thus forming the hollow spherical cap 26 and fixing its dimensions.

Another solution is to inject an adhesive into the space between the free edges 74, 76. The adhesive thus makes it possible to keep the free edges 74, 76 together and to solidify the hollow spherical cap 26 formed. Hardening of the composite piezoelectric material and curing of the adhesive prevent shifting of an angular sector 78 relative to the adjoining angular sectors 78.

FIG. 10 is a perspective view of a hollow spherical cap 26 realized by way of the method in accordance with the invention. In conformity with the method used, the electrode 44 may be formed by closed rings 50, 52 or by rings 50, 52 which have been cut into several angular sectors (in this case four sectors) which correspond to the angular sectors 78. Indeed, as the electrode 44 is realized on the plate 20 before the formation of the cap 26, the cutting of the slits 70 implies cutting of the rings 50 and 52, thus forming ring sectors 50a, 52a, 50b, 52b, 50c , . . . . After the formation of the cap 26, the free ends of the ring sectors 50a, 52a . . . are no longer in contact with the free ends of the adjoining ring sectors.

This enables the realization of two types of ultrasonic transducer.

The realization of the first type of ultrasonic transducer 60 consists in electrically connecting the free ends of the ring sectors to the free ends of the facing ring sectors 50a, 52a . . . in such a manner that electrical continuity is ensured for each ring 50, 52. Thus, each ring 50, 52 of a conductive material can be connected to a current generator 48 via a conductive element 56, 58, respectively, each of which is fed with a current of different phase and/or amplitude. When the phase and/or the amplitude of the current applied to the various rings 50, 52 by the generator 48 differs, the focal distance of the ultrasound transducer 60 is modified.

Figure 12:
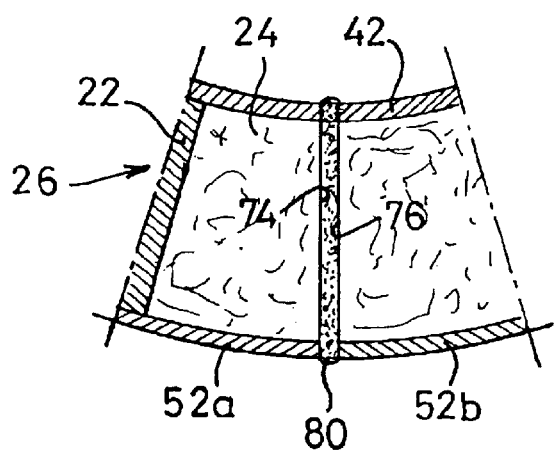
FIG. 12 is a partial sectional view at an increased scale, taken along the line 12—12 in the foregoing Figure.

The realization of the second type of ultrasound transducer 60, as shown in FIG. 11, consists in ensuring that the free ends of the ring sectors 50a, 52a . . . are not in contact with the free ends of the facing ring sectors 50b, 52b . . . . To this end, it is advantageous when the adhesive injected into the slits 70 so as to enhance the rigidity of the spherical cap 26 is an electrically insulating adhesive. Each ring 50, 52 is thus formed by four ring sectors 50a, 52a . . . which are electrically insulated from one another by a band of adhesive 80 which is shown in detail in FIG. 12. In this case each ring sector 50a, 52a . . . is connected to the current generator via an associated conductive element 56a, 58a, 56b, . . . . The generator 48 can supply each ring sector 50a, 52a, . . . with a current of different phase and/or amplitude.

Application of the current difference between the rings 50, 52 thus enables variation of the focal distance of the transducer 60. When the current difference is applied between each ring sector 50a, 52a, . . . , that is, when all ring sectors 50a, 52a situated in an angular sector 78 are fed with identical currents and when the ring sectors situated in the individual angular sectors 78 are different, the orientation of the ultrasound beam can be changed. Thus, the focal spot can be displaced without changing the position and the orientation of the transducer 60.

In accordance with FIG. 11, the part of the electrode 44 which is situated at the apex of the cap 26 may be a disc 82 of an electrically conductive material which is fed via a conductive element 84. The realization of the electrode 44 of the transducer 60 can thus be simplified.

In conformity with a preferred embodiment, for example, for an ultrasound transducer of a diameter of 80 mm, a radius of curvature of 60 mm and a thickness of 1 mm, the spherical cap 26 is realized on the basis of a disc which has a diameter of approximately 85 mm and is provided with eight radial slits 70 which are angularly distributed in a regular fashion. The electrode which is situated on the convex surface of such an ultrasound transducer then comprises 14 rings of a conductive material. Each ring is divided into eight angular sectors. In this case the width of each slit 70 at the area of the peripheral edge 72 is of the order of 2.4 mm. A transducer of this kind can be used as an ultrasound transducer of a power of approximately 200 watts, for example, for the treatment of tumors situated near the skin of the patient, for example, breast tumors. It is to be noted that when use is made of a disc comprising eight radial slits 70, the distribution of the deformation during the formation of the spherical cap 26 will be better, that is, in comparison with a disc comprising only four radial slits 70.

What is claimed is:

1. A method of manufacturing an ultrasound transducer, comprising:

providing a plate shaped as a disc and formed of a composite piezoelectric material;

cutting the plate to form at least one slit in the plate, wherein the at least one slit has a radial orientation and extends from a peripheral edge of the disc towards its center, further wherein the at least one slit includes two facing, oppositely situated free edges which bound the slit; and forming the plate into a hollow spherical cap by deformation, wherein the two facing, oppositely situated free edges which bound the slit are substantially in contact with one another so as to minimize internal stresses in the cap caused by the deformation.

2. The method of manufacturing as claimed in claim 1, wherein the at least one slit extends radially partly along a radius of the disc.

3. The method of manufacturing as claimed in claim 1, wherein the at least one slit extends radially as far as the center of the disc.

4. The method of manufacturing as claimed in claim 1, wherein at least two slits extend radially as far as the center of the disc in such a manner that the disc is separated into at least two distinct portions.

5. The method of manufacturing as claimed in claim 1, wherein the facing, oppositely situated free edges have a radial orientation in such a manner that the corresponding slit forms a V whose apex is oriented towards the center of the disc.

6. The method of manufacturing as claimed in claim 5, wherein the oppositely situated free edges are curved and convex, further wherein their convexity is opposed to one another.

7. The method of manufacturing as claimed in claim 1, wherein cutting the plate to form at least one slit further includes forming a series of slits which are angularly distributed in a regular fashion so as to define substantially identical angular sectors.

8. The method as claimed in claim 1, further comprising:

introducing an adhesive into the at least one slit, wherein after the step of forming, the oppositely situated free edges are glued to one another.

9. The method as claimed in claim 8, wherein the adhesive is an electrically insulating adhesive.

10. The method of manufacturing as claimed in claim 1, wherein during the step of forming, the composite piezoelectric material is heated so as to soften it, after which it is cooled so as to fix its dimensions.

11. An ultrasound transducer in the form of a hollow spherical cap and including at least one slit having a radial orientation, the ultrasound transducer produced by the method of:

providing a plate shaped as a disc and formed of a composite piezoelectric material;

cutting the plate to form at least one slit in the plate, wherein the at least one slit has a radial orientation and extends from a peripheral edge of the disc towards its center, further wherein the at least one slit includes two facing, oppositely situated free edges which bound the slit; and forming the plate into a hollow spherical cap by deformation, wherein the two facing, oppositely situated free edges which bound the slit are substantially in contact with one another so as to minimize internal stresses in the cap caused by the deformation.

* * * * *